US012626821B2

(12) United States Patent
Gerner et al.

(10) Patent No.: US 12,626,821 B2
(45) Date of Patent: May 12, 2026

(54) SYSTEMS AND METHODS FOR AUTOMATIC BENCHMARKING FOR RADIOLOGY

(71) Applicant: GE Precision Healthcare LLC, Wauwatosa, WI (US)

(72) Inventors: Philippe Gerner, Strasbourg (FR); Estelle Spasic, Metz (FR); María del Pilar Pujadas, Madrid (ES); Hugo Laullier, Montpellier (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 149 days.

(21) Appl. No.: 18/188,990

(22) Filed: Mar. 23, 2023

(65) Prior Publication Data

US 2024/0321464 A1 Sep. 26, 2024

(51) Int. Cl.
*G16H 50/50* (2018.01)
*G16H 10/20* (2018.01)
(Continued)

(52) U.S. Cl.
CPC ............. *G16H 50/50* (2018.01); *G16H 10/20* (2018.01); *G16H 10/60* (2018.01); *G16H 50/70* (2018.01)

(58) Field of Classification Search
CPC ........ G16H 50/50; G16H 10/20; G16H 10/60; G16H 50/70; G16H 50/20; G16H 30/40; G16H 40/63; G16H 20/40
See application file for complete search history.

(56) References Cited

U.S. PATENT DOCUMENTS

2007/0032733 A1* 2/2007 Burton ................. A61B 5/7264
600/509
2015/0317337 A1 11/2015 Edgar
(Continued)

FOREIGN PATENT DOCUMENTS

EP          3451210 B1    3/2021
EP          3628233 B1    6/2021
WO     WO-2020023961 A1 *   1/2020   ............... A61N 5/10

OTHER PUBLICATIONS

Kapoor et al., Infrastructure tools to support an effective Radiation Oncology Learning Health System, Jul. 19, 2023, Journal of Applied Clinical Medical Physics, pp. 1-19. (Year: 2023).*
(Continued)

*Primary Examiner* — Christopher L Gilligan
(74) *Attorney, Agent, or Firm* — McCoy Russell LLP

(57) ABSTRACT

Various methods and systems are provided for a medical system, comprising a client device having a graphical user interface (GUI) and a display device, the client device operably coupled to a network, and an analytics tool configured with instructions stored on a memory and executable by a processor to receive a first user input via the client device, identify values of at least one variable of interest (VOI) from a subject of a benchmark target variable which differ by at least a first threshold amount from other values of the same VOI from other subjects of the benchmark target variable within a benchmarking context, generate and output for display on the display device a causal graph illustrating influences of different study variables on an identified VOI value, and automatically update the causal graph and display thereof based on a second user input to adjust at least one study variable.

9 Claims, 11 Drawing Sheets

(51) Int. Cl.
  *G16H 10/60*     (2018.01)
  *G16H 50/70*     (2018.01)

(56) References Cited

U.S. PATENT DOCUMENTS

| | | | |
|---|---|---|---|
| 2015/0356258 A1 | 12/2015 | Moore | |
| 2017/0177822 A1* | 6/2017 | Fogel | G16H 50/20 |
| 2019/0131016 A1* | 5/2019 | Cohen | A61B 6/032 |
| 2020/0030632 A1* | 1/2020 | Munbodh | A61N 5/1071 |
| 2020/0069277 A1 | 3/2020 | Dorn | |
| 2020/0135303 A1* | 4/2020 | Barber | G16B 25/10 |
| 2022/0114417 A1 | 4/2022 | Dalli | |
| 2023/0360777 A1* | 11/2023 | Scherrer | G16H 40/67 |
| 2024/0331803 A1* | 10/2024 | Siebert | G16B 15/20 |

OTHER PUBLICATIONS

Luo et al., Balancing accuracy and interpretability of machine learning approaches for radiation treatment outcomes modeling, Jun. 25, 2019, BJR Open, pp. 1-12. (Year: 2019).*

EP application 24160479.2 filed Feb. 29, 2024—extended Search Report issued Aug. 26, 2024; 10 pages.

Bedez, M. et al., "Methods and Systems for Automatic CT Image Quality Assessment," U.S. Appl. No. 63/384,383, filed Nov. 18, 2022, 46 pages.

* cited by examiner

700

Causal graph for CT case:

SYSTEMS AND METHODS FOR AUTOMATIC BENCHMARKING FOR RADIOLOGY

TECHNICAL FIELD

Examples of the subject matter disclosed herein relate to automatic imaging protocol parameter adjustment based on radiation analytics.

BACKGROUND

In some radiation dose management systems, a user may explore how factors impacting a radiation dose received by a patient compare between protocols, devices, operators, and so on. However, if the user wants to compare only similar studies (e.g., studies captured using the same or similar study variables), the user has to manually sort through data based on chosen stratifications of the studies (e.g., by BMI range, by age range). Additionally, in conventional dose management solutions, a user may manually search for parameters which could explain differences in received radiation dose among studies. Attempts to adjust a radiation dose received by a patient may include adjusting one or more parameters which may influence the radiation dose, and repeating the scan.

SUMMARY

The current disclosure at least partially addresses one or more of the above identified issues by a medical system which may be used for radiation dose management, the medical system comprising a client device having a graphical user interface (GUI) and a display device, the client device operably coupled to a network, and an analytics tool configured with instructions stored on a memory and executable by a processor to receive a first user input via the client device, identify values of at least one variable of interest (VOI) from a subject of a benchmark target variable which differ by at least a first threshold amount from other values of the same VOI from other subjects of the benchmark target variable within a benchmarking context, generate and output for display on the display device a causal graph illustrating influences of different study variables on an identified VOI value, and automatically update the causal graph and display thereof based on a second user input to adjust at least one study variable.

A method for the analytics tool may include comparing a VOI value from a first subject of a benchmark target variable with values of the same VOI from other subjects of the same benchmark target variable within a benchmarking context, identifying a VOI value which differs from a comparable VOI value by at least a first threshold, generating at least one candidate explanation for the difference in VOI values, generating a causal graph illustrating at least one candidate explanation for the difference in VOI values, and automatically updating the causal graph to incorporate adjustments to nodes of the causal graph to simulate a radiation dose delivery.

The current disclosure further at least partially addresses one or more of the above identified issues using a method, comprising receiving a first user input, including selection of at least one variable of interest (VOI), a benchmark target variable, and a benchmarking context, for the at least one VOI, comparing values of the VOI for a first subject of the benchmark target variable with values of the same VOI from other subjects of the benchmark target variable within the benchmarking context to identify VOI values which differ by at least a first threshold amount from other VOI values of the same VOI, for the VOI values identified as differing by at least the first threshold amount, generating and outputting for display an output including a subject identifier and at least one candidate explanation for the identified VOI value, receiving a second user input selecting a subject from the output by selecting the respective subject identifier, comparing study variables used to generate the identified VOI value to average values of respective study variables of comparable VOI values, and generating and outputting for display a causal graph indicating at least one study variable of the study variables used to generate the identified VOI which differs by at least a second threshold amount, receiving a third user input including an adjustment to at least one study variable of the causal graph, wherein adjustment includes adding and/or removing at least one study variable node, and/or adjusting a value of the at least one study variable node, updating the causal graph based on adjustments included in the third user input, and outputting the updated causal graph for display on a display device.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
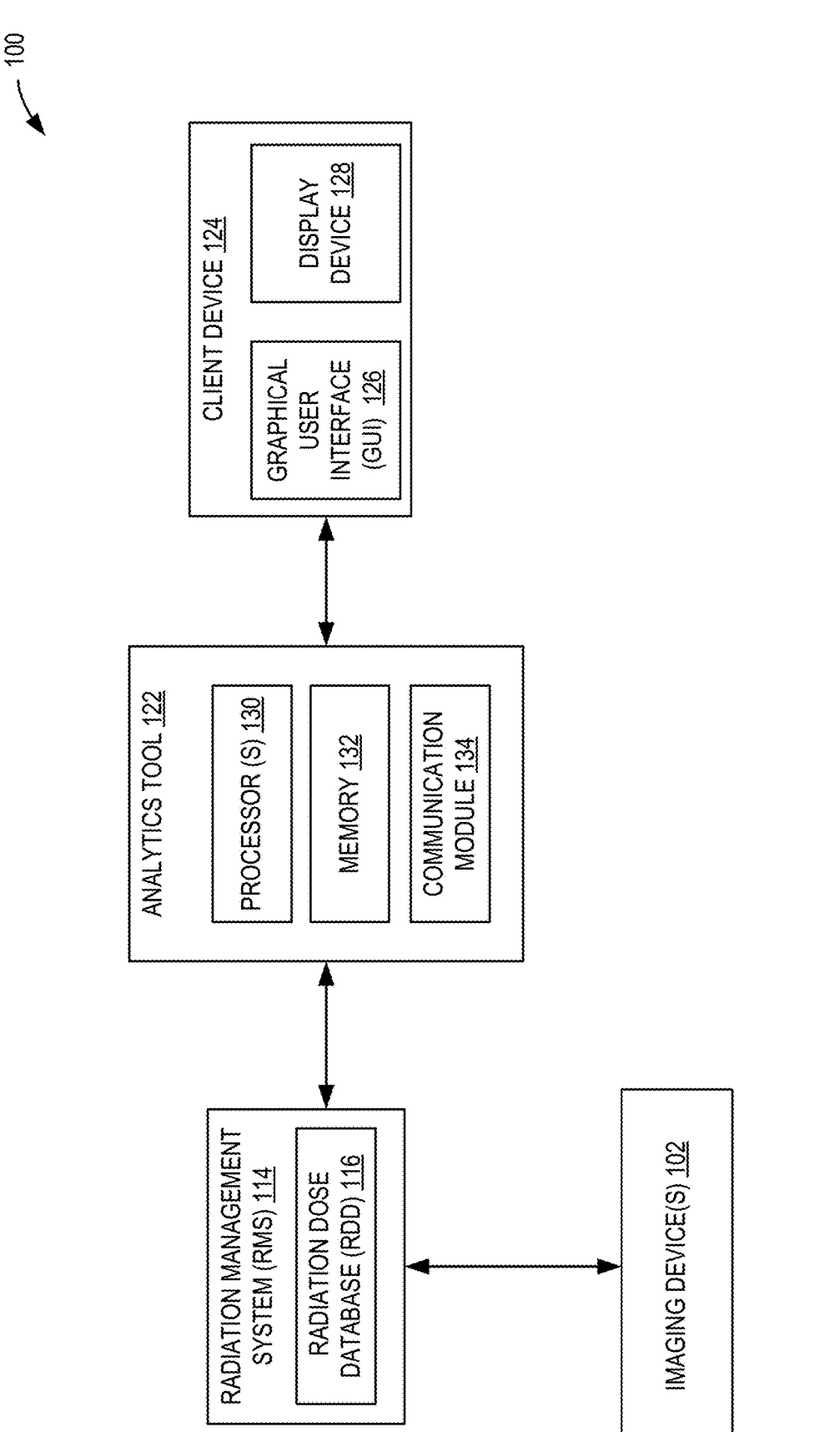
FIG. 1 shows a schematic block diagram of a radiation dose management system.

Described herein are systems and methods for automating radiation dose management using a tool which performs an assessment of received radiation dose among study parameters. Study parameters may be selected by a user and the tool may automatically compare radiation dose values within the selected study parameters. For example, the tool compares values of a variable of interest (VOI) for a first subject of a benchmark target variable with values of the same VOI from other subjects of the benchmark target variable within a benchmarking context to identify VOI values which differ by at least a first threshold amount from other VOI values of the same VOI. The VOI is representative of a radiation dose (e.g., a radiation dose metric), and may be a dose length product (DLP), a computed tomography dose index (CTDI), a size specific dose estimate (SSDE), and/or an image quality related to a radiation dose. The benchmark target variable may define a population whose VOI values are compared. For example, the benchmark target variable may be operators, hospitals, devices and so on, and a benchmark target variable subject is an individual entity of the benchmark target variable (e.g., a first operator, a second operator, and so on). When the benchmark target variable is "operators", VOI values (e.g., DLP values) from scans performed by different operators within a given context may be compared, as further described herein. The benchmarking context defines a target set of historical studies to be compared. The benchmarking context may be defined as a timeframe (e.g., within the past three years), as a distance (e.g., healthcare providers within a 50-mile radius), an amount of locations and/or devices (e.g., three hospitals) and so on. For example, VOI values (e.g., DLP values) from different benchmark target variable subjects (e.g., from scans performed by different operators) within the past year may be compared to identify instances of high radiation doses. The tool enables automatic determination of which one or more subjects of the benchmark target variable deliver a greater radiation dose to patients, compared to peer subjects of the same benchmark target variable. The tool further provides some candidate explanations for the difference and visual depictions of relationships among study variables which may influence differences in radiation dose among benchmark target variable subjects.

Dose index registries including radiation dose data are typically held at a national level and allow for comparison of dose averages for comparable studies between hospitals. The systems and methods described herein adds to current uses of dose registries a versatility of benchmark target variables, automatic matching of similar studies, and the possibility to use the same method for a single hospital for internal benchmarking.

In this way, medical providers may automatically evaluate where adjustments may be made to radiology practices, which may reduce a workload and/or time spent on dose-level inspections, compared to a manual comparison of the devices, operators, protocols, and so on. Also, when the tool is used to compare among hospitals/sites (e.g., automatically pinpoint areas of difference), the customer (e.g., hospital/site) may compare its practices against other hospitals, when protocol normalization is included. The tool may thus assist a healthcare provider in identifying best-practices (e.g., practices which result in a desired radiation dose level). Benchmarking on operators, devices, protocols, and so on cases personnel training. In this way, identification of study variables which influence radiation dose levels among different operators, devices, protocols, and so on may highlight opportunities where practices may be adjusted so a desirable dose is delivered to a patient.

Figure 2:
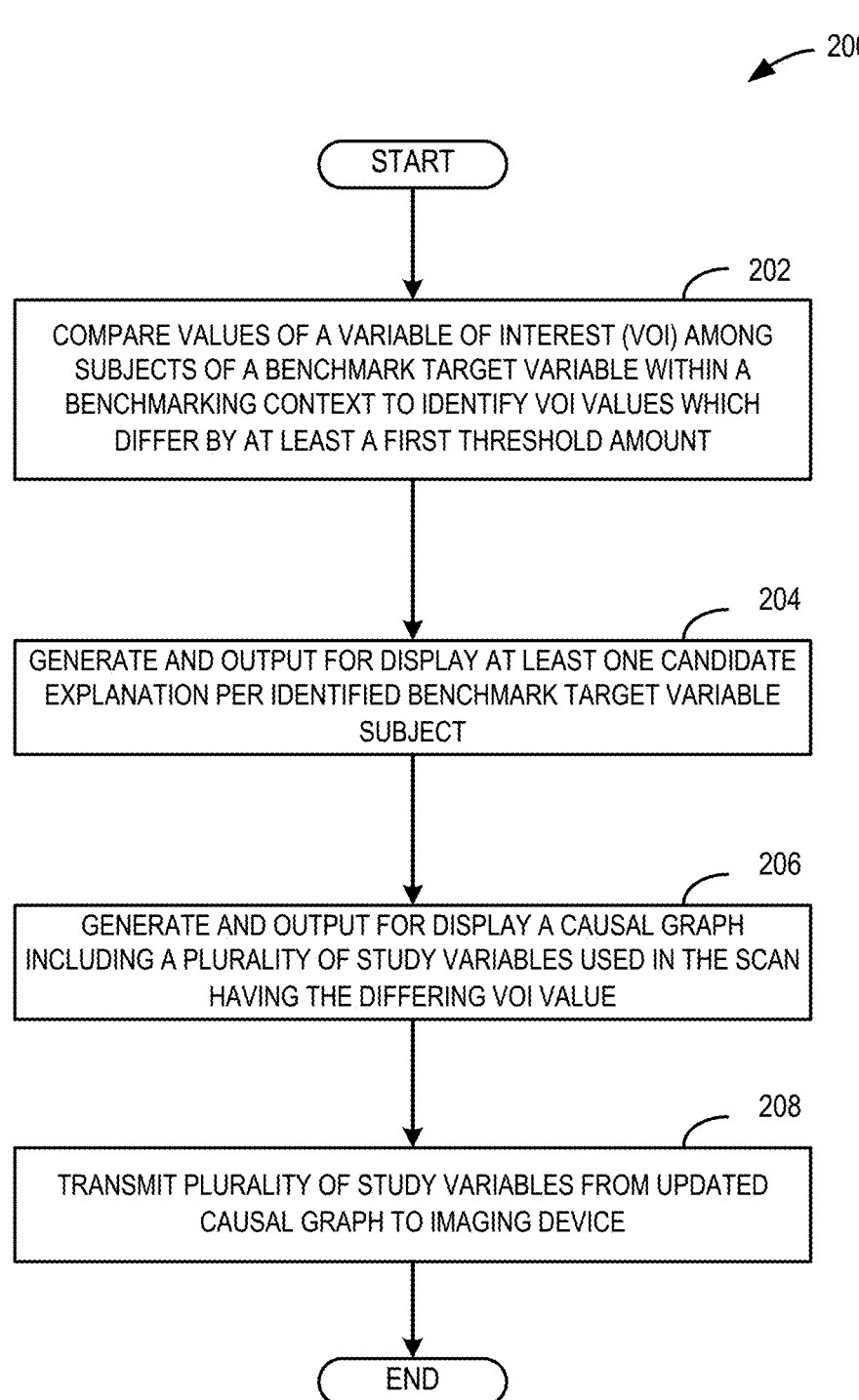
FIG. 2 illustrates a high-level method for identifying and analyzing instances of high radiation dose.
Figure 3:
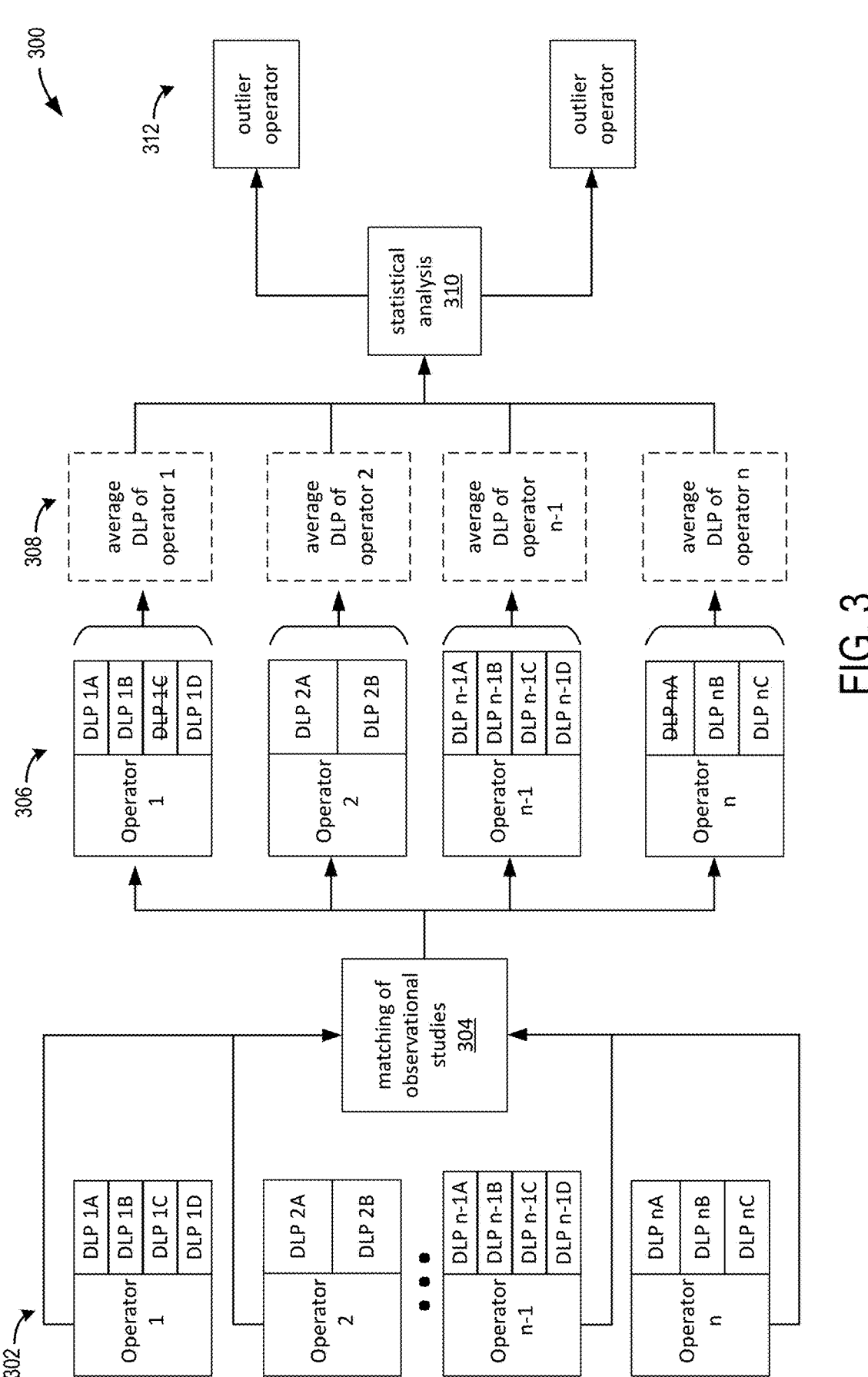
FIG. 3 shows a first example strategy for comparison variables of interest (VOI) among benchmark target variable subjects within a benchmarking context.
Figure 4:
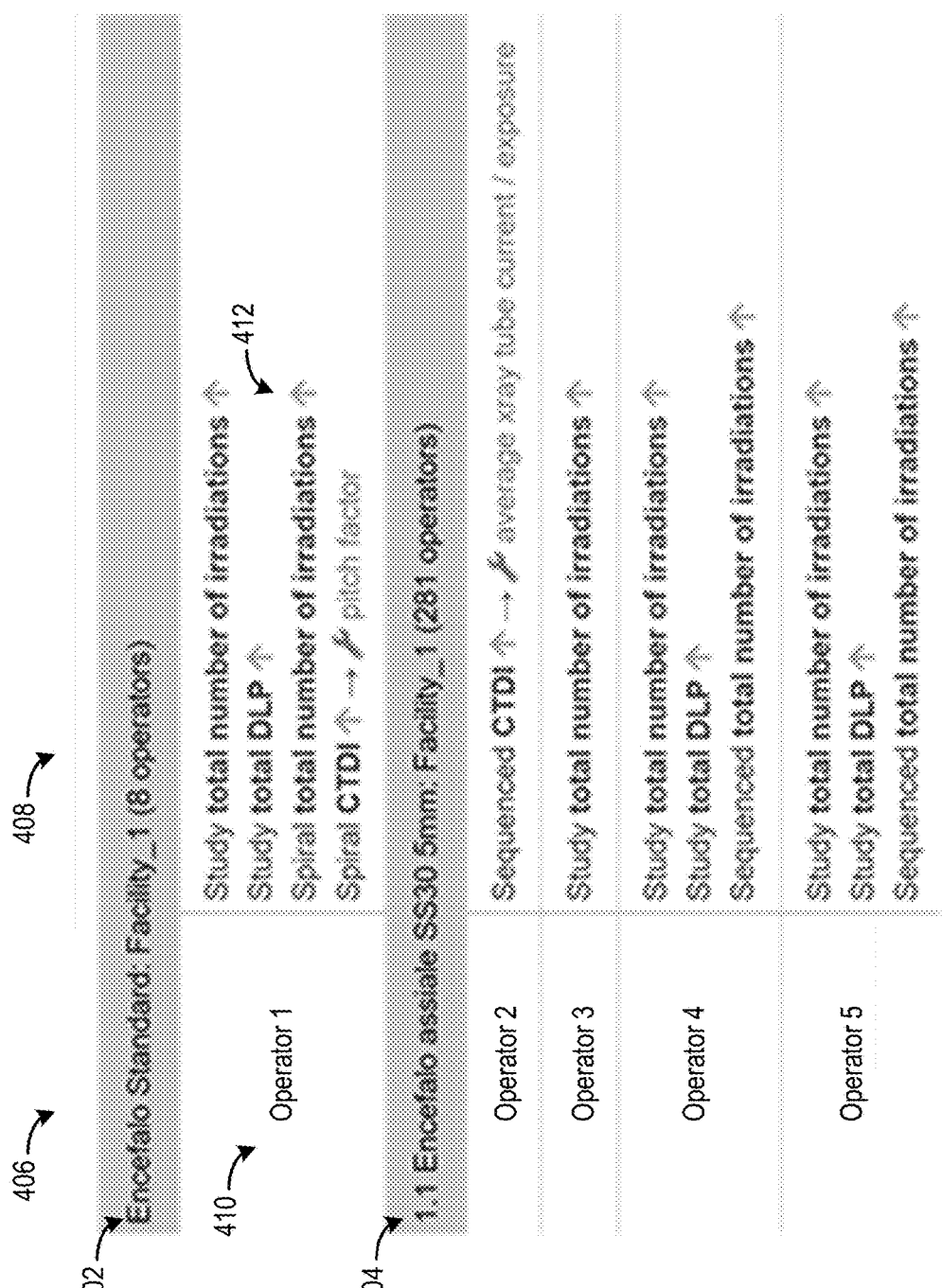
FIG. 4 shows an example display which includes information of benchmark target variable subjects which have high VOI values.
Figure 5:
FIG. 5 shows a causal graph illustrating influence of study variables on VOI values.
Figure 5:
Figure 7:
FIG. 7 shows a first example updated causal graph based on removal of a study variable from the causal graph of FIG. 5.
Figure 7:
Figure 8:
FIG. 8 shows a second example updated causal graph based on addition of a study variable to the causal graph of FIG. 5.
Figure 8:
Figure 9:
FIG. 9 shows a third example updated causal graph based on adjustment of at least one study variable value of the causal graph of FIG. 5.
Figure 10A:
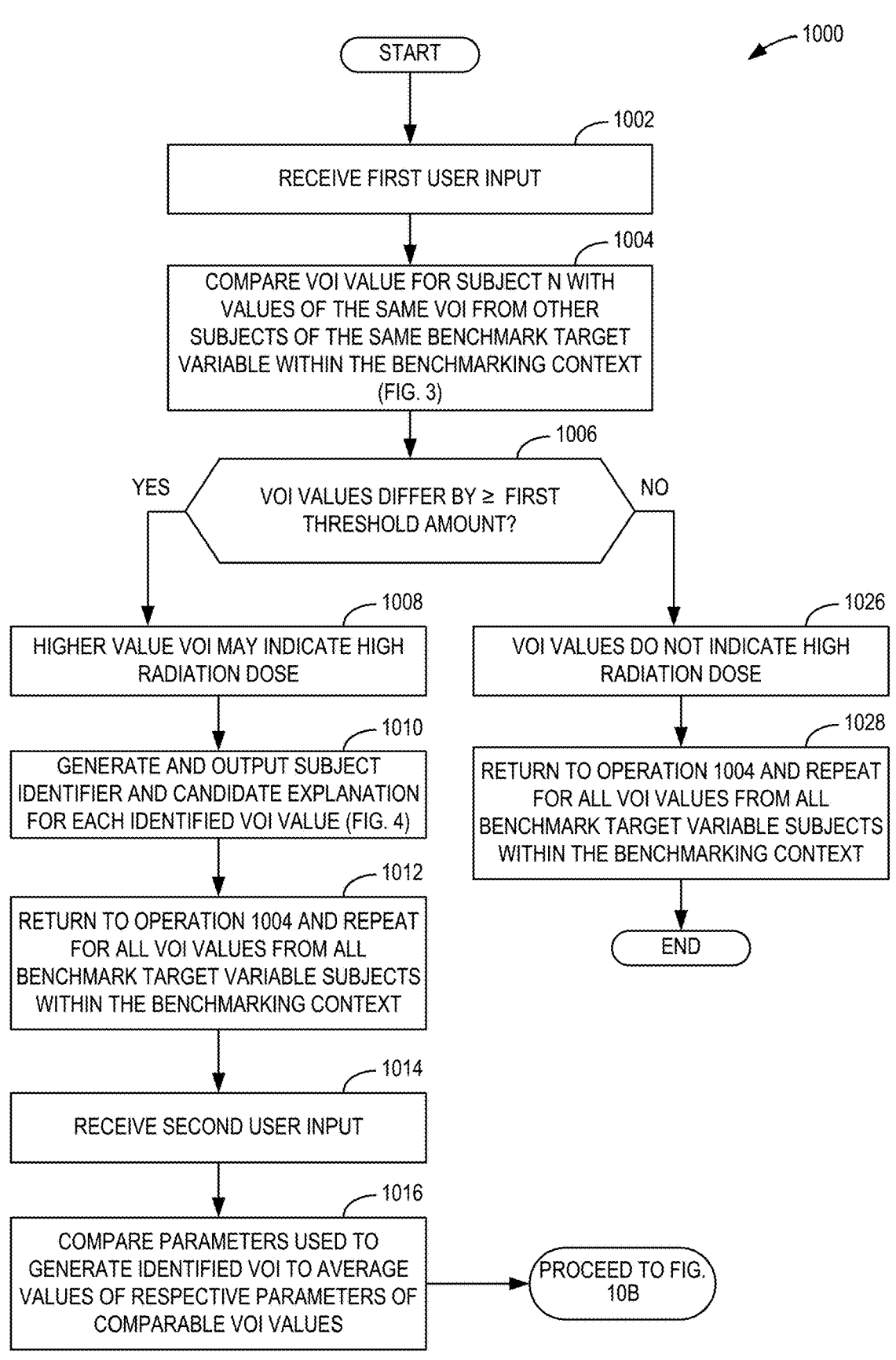
FIGS. 10A-10B illustrate a method for identifying instances of high radiation dose, generating candidate explanations, and generating and automatically updating causal graphs.
Figure 10B:
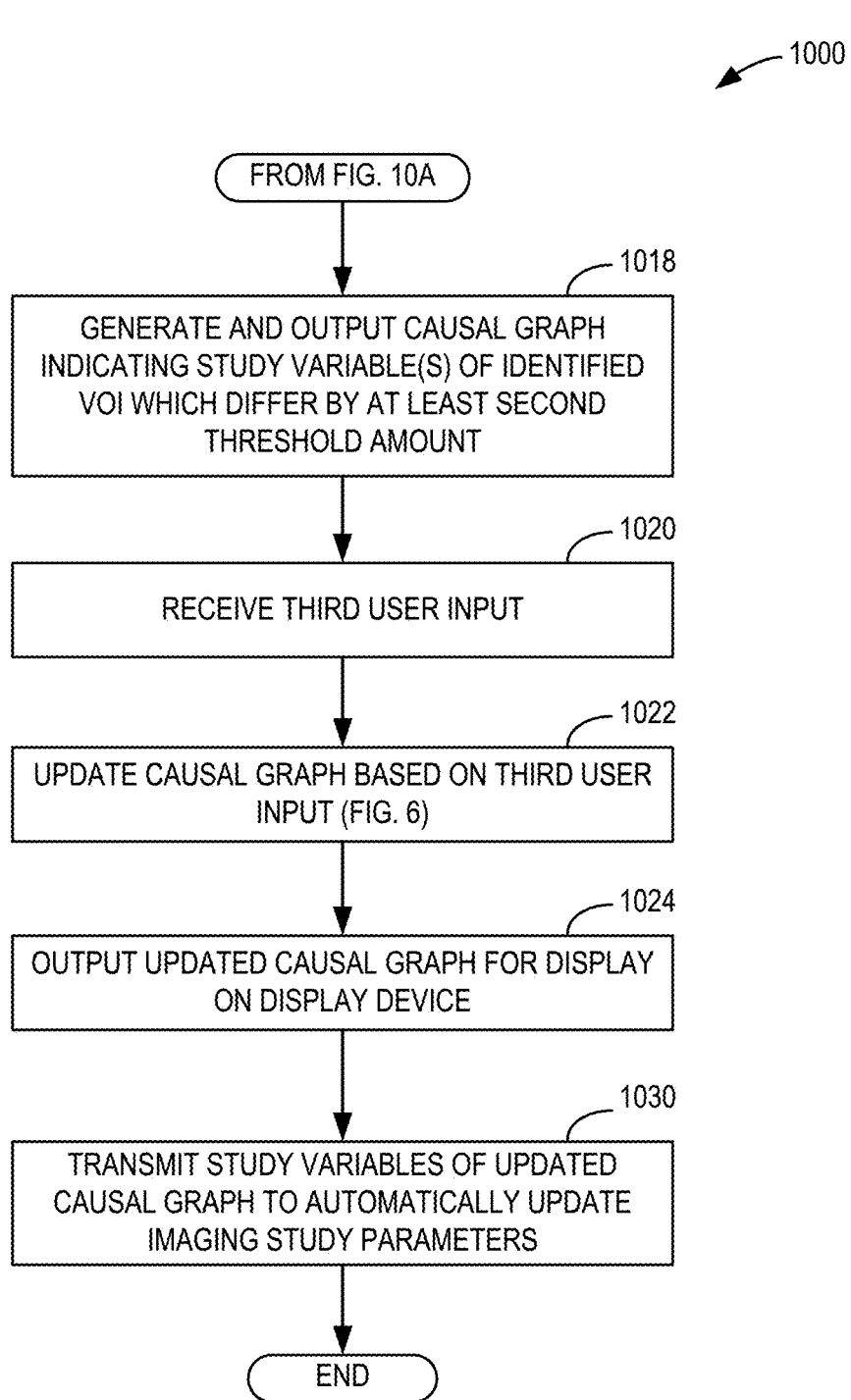

FIG. 1 shows a block diagram illustrating a system 100 for medical data transmission and analytics, including an analytics tool which may store and execute instructions for a method for identifying instances of high radiation dose in radiation dose data. A high-level example of the method for identifying instances of high radiation dose, as well as generating candidate explanations and a display illustrating influences of study variables on radiation dose is shown in FIG. 2. A detailed method for identifying instances of high radiation dose, identifying candidate explanations, and generating and automatically updating causal graphs is illustrated in FIGS. 10A-10B. FIG. 3 shows a first example strategy for comparing variable of interest (VOI) values. Information regarding benchmark target variable subjects which are identified as generating VOI values which differ from VOI values of peer subjects of the same benchmark target variable by at least a first threshold amount is output for display, an example of which is shown in FIG. 4. The display may be used to select a benchmark target variable subject to further analyze. FIG. 5 shows a causal graph illustrating influence of study variables on VOI values, for example, of a selected benchmark target variable subject. The causal graph of FIG. 5 may be manipulated to simulate effects of different study variables on a VOI value, as described in the high-level method of FIG. 6. FIG. 7 shows a first example updated causal graph based on removal of a study variable from the causal graph of FIG. 5, FIG. 8 shows a second example updated causal graph based on addition of a study variable to the causal graph of FIG. 5, and FIG. 9 shows a third example updated causal graph based on adjustment to a study parameter value of the causal graph of FIG. 5.

FIG. 1 shows a block diagram illustrating a system 100 for medical data transmission and analytics. The system 100 may be used to transmit medical data, collected by a hospital modality and stored in a medical database, to an analytics tool. In the examples described herein, medical data which is transmitted by the medical data transmission system may be related to a radiation procedure performed by hospital modalities such as imaging systems, however the methods and systems described herein may also be applied for other types of medical data collected by other modalities.

An imaging device 102 may be a hospital modality, such as a computed tomography (CT) system or an x-ray angiography (XA) system. The imaging device 102 may perform imaging procedures, such as radiation observations in which a patient is exposed to a radiation dose. The imaging device 102 may share data collected by a respective modality to a storage device via at least one of multiple connectivity methods. The multiple connectivity methods may include (e.g., Digital Imaging and Communications in Medicine (DICOM®) images, DICOM® SRs, Health Level Seven (HL7®), proprietary logs associated with a manufacturer or operating system, and so on. The imaging device 102 may be operably coupled to a medical database and/or storage device via a wired connection, a wireless connection, and/or any method for communicably connecting systems. As described herein "operably coupled" is to be understood as coupling of elements via connectivity methods (e.g., wired connection, wireless connection, and so on) which enable transfer of data, signals, requests, and/or other information among the operably coupled elements.

In the example described herein, the medical database to which the imaging device 102 is operably coupled is a radiation dose database (RDD) 116 of a radiation dose management system (RMS) 114. The RDD 116 is configured to receive radiation dose data from at least one imaging device 102 and store the radiation dose data. The RDD 116 may be an external database or a local database (e.g., housed on a device of the system 100) of the RMS 114. The RDD 116 may be a database stored in a mass storage device configured to communicate with secure channels (e.g., HTTPS and TLS), and store data in encrypted form. As further described herein, the imaging device 102 may share radiation dose data to the RMS 114, and the RMS 114 may enrich the RDD 116 with data collected from exams performed by the respective hospital modality (e.g., radiation dose data), as well as other exam and/or hospital modality data (e.g., hospital modality manufacturer, hospital modality operator, and so on). The RMS 114 may be further configured with instructions stored on memory and executable by a processor to enable tracking of radiation doses received by a patient over time.

The RMS 114, and specifically the RDD 116, is communicably coupled to an analytics tool 122 to allow transfer of radiation dose data therebetween. The radiation dose data may include a summary of an imaging procedure (e.g., study variables), radiation dose administered to a patient, and so on. In some examples, the analytics tool 122 may be integrated in the RMS 114. The RMS 114 may be configured to expose defined resources, thus exposing radiation dose data through the analytics tool 122, where the analytics tool 122 may enhance third-party usage of data.

The RMS 114 may be configured to receive and store radiation dose data from at least one imaging device 102. For example, the RMS 114 may be configured to implement resources including: a CT radiation dose summary, an X-ray radiation dose summary, a radiopharmaceutical radiation dose summary, a CT irradiation event summary, a practitioner, a modality device, an imaging study, and a patient. Other additional or alternative resources may be included, such as patient body mass index (BMI) and patient weight observation. In some examples, the analytics tool 122 may be configured to collect radiation information following requests of the consuming applications. Radiation information may be distributed among different resources of the analytics tool 122.

As described herein, the analytics tool 122 is configured to use defined resources (e.g., radiation dose data) for macroscopic analysis of radiation dose data. This may be used for comparison between devices, cohorts of patients, or comparison between hospitals regarding national radiation dose levels, for example. For example, the analytics tool 122 may be configured to enable visualization, analysis, analytics, and transformation of data. Data may be collected from multiple sources and aggregated and presented for query and analysis. The analytics tool 122 may enable creation of dashboards based on collected data, which allow users to select metrics and cohort levels to aggregate data in selected cohorts and groups, providing a macroscopic view of the data for analysis, such as detection of anomalies, as described herein with respect to FIGS. 2-10B.

The analytics tool 122 may be communicably coupled to one or more client devices 124 for display, manipulation, and visualization of analytics on the radiation dose data. Each client device may include a processor, memory, communication module, user input device, display (e.g., screen or monitor), and/or other subsystems and may be in the form of a desktop computing device, a laptop computing device, a tablet, a smart phone, or other device. The client devices may be located locally at the hospital (e.g., as part of hospital administration) and/or remotely from the hospital (such as a user's mobile device). In some examples, the analytics tool 122 may be integrated in the client device 124. When requested, a report generated by the analytics tool 122 may be output for display on a display device of a client device as one or more graphical user interfaces. For example, the client device 124 may be configured with a graphical user interface (GUI) 126 and a display device 128. As an example, the client device 124 may store one or more GUI templates in memory that include placeholders for relevant information transmitted to the client device 124 from the analytics tool 122.

The analytics tool 122 may be configured with resources including a processor 130, a memory 132, and a communication module 134 that may be allocated to store and execute one or more of the methods described herein. Elements of the system 100 may communicate with each other via a network, which may be a suitable wired and/or wireless network. One or more of the devices described herein may be implemented over a cloud or other computer network.

Communication module 134 facilitates transmission of electronic data within and/or among one or more systems. Communication via communication module 134 can be implemented using one or more protocols. In some examples, communication via communication module 134 occurs according to one or more standards DICOM®, HL7®, ANSI X12N, and so on. Communication module 134 can be a wired interface (e.g., a data bus, a Universal Serial Bus (USB) connection, etc.) and/or a wireless interface (e.g., radio frequency, infrared, near field communication (NFC), etc.). For example, communication module 134 may communicate via wired local area network (LAN), wireless LAN, wide area network (WAN), etc. using any past, present, or future communication protocol (e.g., BLUETOOTH™, USB 2.0, USB 3.0, etc.). Memory 132 includes one or more data storage structures, such as optical memory devices, magnetic memory devices, or solid-state memory devices, for storing programs and routines executed by processor(s) 130 to carry out various functionalities disclosed herein. Memory 132 may include any desired type of volatile and/or non-volatile memory such as, for example, static random access memory (SRAM), dynamic random access memory (DRAM), flash memory, read-only memory (ROM), etc.

Processor(s) 130 may be any suitable processor, processing unit, or microprocessor, for example. Processor(s) 130 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

FIG. 2 shows a high-level flow chart illustrating a method 200 for identifying instances of high radiation dose, generating candidate explanations for potential causes of the instances of high radiation dose, and simulating instances which may alter radiation dose based on adjustment of study variables which may influence the radiation dose. Instances of high radiation dose as defined herein include instances where a first radiation dose value and a second radiation dose value differ by at least a first threshold amount. For example, a first threshold amount may be an amount of radiation which, when added to a desired radiation dose, increases a total radiation dose to above a desired level, where degradation may occur above the desired level. In some examples, the first threshold may represent a statistically significant difference in values. When the first radiation dose value and the second radiation dose value differ by at least the first threshold amount, the radiation dose having a higher value is identified as having high radiation, and is further analyzed according to the methods described herein. Instructions for the method 200, and the other methods described herein, may be stored in a memory of an analytics tool, such as the memory 132 of the analytics tool 122 of FIG. 1, and executed by a processor thereof (e.g., the processor 130). The processor 130 may receive inputs/requests/selections, as described herein, which may be input by a user via a GUI (e.g., the GUI 126 of the client device 124 of FIG. 1).

At 202, the method 200 includes comparing values of a variable of interest (VOI) for a first subject of a benchmark target variable with values of the same VOI from other subjects of the benchmark target variable within a benchmarking context to identify VOI values which differ by at least a first threshold amount from other VOI values of the same VOI. For example, VOI values (e.g., DLP values) from different benchmark target variable subjects (e.g., from scans performed by different operators) within the past year may be compared to identify instances of high radiation doses. As another example, when the VOI is CTDI, the benchmark target variable is devices, and the benchmarking context is three hospitals, CTDI values from scans performed using different devices from three different hospitals may be compared to identify instances of high radiation doses. In some examples, a stratification variable may be selected by a user to further specify the benchmarking context, such that the method 200 is applied to each stratum of the benchmark target variable. For example, as further described with respect to FIG. 4, the method 200 may be used to compare protocols (e.g., identified by the stratification variable) performed by operators (e.g., the benchmark target variable).

Comparing values of a VOI may be performed using matching of observational studies and statistical analysis, as further described with respect to FIG. 3. Briefly, comparing values of a VOI includes matching a first VOI value (e.g., DLP, CTDI, and so on) for a first subject of the benchmark target variable (e.g., an operator, a procedure, and so on) to comparable values, for example, a VOI value from a patient scan having similar study variables (e.g., patient age, size, gender, and so on) to the study variables of the first VOI value. Following matching of observational studies, statistical analysis such as a student's t-test is performed to identify VOI values which differ by at least the first threshold amount. Comparison of VOI values may be performed for each scan performed by each subject of the benchmark target variable within a benchmarking context.

The method 200 includes identifying candidate explanations which may help explain why at least one VOI value from a benchmark target variable subject differs from other VOI values from other subjects of the benchmark target variable within a benchmarking context which have similar study variables. At 204, the method 200 includes generating and outputting for display at least one candidate explanation per identified benchmark target variable subject. Candidate explanations may include analyses about parameters of the protocol used to capture the VOI value, characteristics of the device used to perform the protocol, and/or patient characteristics. For example, information regarding relationships among study variables of an imaging study and values of the study variables which result in an identified VOI value may be evaluated to identify one or more study variable values which may directly influence the VOI value. Each possible candidate explanation (e.g., identifying one or more study variables) may be examined, and matching may be applied so the effect of the study variable on the VOI may be evaluated by comparing values of one or more study variables to comparable studies. As further described herein, a study variable may be identified as the candidate explanation for a given VOI value when the study variable has a statistically significant effect on the VOI. For example, the study variable may differ from other comparable study variables by at least a second threshold amount. In another example, the statistically significant effect may be that the VOI value differs from other VOI values from comparable studies by at least a first threshold amount. An example display is shown and further described with respect to FIG. 4. The display may include some or all subjects of the benchmark target variable within a benchmarking context which have been identified as having differing VOI values.

One or more candidate explanations for a differing VOI value may be further analyzed using a causal graph, which may also be used to simulate an effect of adjusting study variables on the VOI value. At 206, the method 200 include generating and outputting for display a causal graph including a plurality of study variables used in the scan having the differing VOI value. Study variables of the causal graph may include patient characteristics (e.g., age, size, weight), device characteristics such as make and model, operator, protocol, and parameters of the protocol. When displayed, the causal graph may be manipulated, for example by a user. Nodes of the causal graph, each of which represent a factor of the plurality of study variables, may be added and/or removed, and the causal graph may be automatically updated to reflect the addition and/or removal of one or more nodes. In some examples, study variables of the causal graph may be adjusted without addition/removal, for example, adjusting parameter values. Automatic updating of the causal graph includes simulating a scan using the adjusted parameter values and nodes which are still included in the causal graph to generate a predicted VOI value based on the updated causal graph. An example causal graph is shown and further described with respect to FIGS. 5-7. In other examples, a causal forest may be used to illustrate potential influences of study variables, where study variables which may directly influence the VOI value are at a top of a tree of the causal forest. The causal graph shows relationships among the study variables, and simulation of scans and dynamic updating of the causal graph may illustrate candidate explanations of differing VOI values, as well as potential study variables which may be implemented in real scans to achieve a desired VOI value.

Adjusted parameter values and study variables (e.g., addition/removal of nodes) of an updated causal graph may be used as parameters for an imaging study. At 208, the method 200 includes transmitting the plurality of study variables from an updated causal graph to an imaging device. In some examples, the plurality of study variables may be transmitted to the imaging device via a memory or other storage, for example, the plurality of study variables may be stored in the RDD 116 of FIG. 1 and retrieved from the RDD 116 by an imaging device of the imaging devices 102. The adjusted parameter values and study variables may be different from parameter values and study variables used to conduct the imaging scan of the identified VOI (e.g., which differs from other VOI values by at least the first threshold amount), therefore using the adjusted parameter values to conduct an imaging scan may result in an adjusted VOI (e.g., increased or decreased VOI value).

Details of the method 200 are now to be discussed in further detail. As described above, comparing values of a VOI may be performed using matching of observational studies and statistical analysis. Different methods of comparison may be used depending on selected VOI, benchmarking target variable, and benchmarking context. Matching of observational studies may include automatically correcting for study variables which may directly and/or indirectly influence the VOI values. For example, when comparing two devices with a given protocol (e.g., the benchmark target variable is "devices" and the benchmarking context is the two devices), each device may have a different patient population. Each of the patient populations may be comprised of a different number of patients and/or patients having different characteristics. To perform a comparison between comparable VOI values of the two devices, each patient (e.g., and associated VOI value) from one device may be matched to a comparable patient (e.g., and respective VOI value), where comparable patients have the same or similar study variables. Study variables may include patient characteristics (e.g., size, age, and weight), series type, device, and protocol.

In some embodiments, VOI values are compared by generating all one-to-one combinations of VOI values among benchmark target variable subjects within the benchmarking context and performing statistical analysis to identify differences in VOI values which differ by at least the first threshold amount. Each VOI value may be individually matched to a VOI value from another subject which has the same or similar study variables. VOI values which do not have a corresponding VOI value from another subject may not be compared to another VOI value and may not be included in the output indicating differing VOI values (e.g., as further described with respect to FIG. 4). Though two or more VOI values may be generated by a study which uses the same or similar study variables, the VOI values themselves may be similar or may be different.

In some embodiments, an average of VOI values for each subject of the benchmark target variable is compared to average VOI values of the other benchmark target variable subjects. Prior to averaging VOI values for each benchmarking target variable subject, each VOI value for a subject may be individually compared to all VOI values for other subjects of the benchmark target variable within the benchmarking context to determine if there is a comparable VOI value, as described above. If a VOI value of a subject is identified which does not have a comparable VOI value from other benchmark target variable subjects, the VOI value may be excluded from the average VOI value, in some examples. VOI values for each subject in the benchmarking context may be averaged, such that each subject has an associated average VOI. By averaging VOI values and removing VOI values generated from different study variables, comparisons of radiation dose among subjects may be made between comparable datasets.

For example, in one year, a first operator may have performed 300 studies. Matching of observational studies includes identifying 300 studies from the other operators in the one-year timeframe which are comparable (e.g., the same or similar study variable values) to the studies of the first operator. This is repeated for each operator in the benchmarking context (e.g., second operator, third operator, n–1 operator, n operator). Matching studies for the first operator (or second/third/etc.) are sourced from a pool of studies for all operators in the benchmarking context (e.g., stored in a radiation dose database, such as the RDD 116 of FIG. 1) to have a greater likelihood of finding comparable studies. For example, an imaging device may have eleven operators in one year. Each of the operators may have performed 300 studies. Comparing studies of the first operator to the pool of studies for all operators includes finding a comparable study for each of the 300 studies of the first operator from the pool of 3000 studies from all operators (e.g., excluding the first operator). This ensures robustness of comparison, compared to doing a 1:1 comparison with another operator (e.g., matching the 300 studies of the first operator with the 300 studies of the second operator).

After identifying comparable VOI values, whether individual VOI values or averaged VOI values, statistical analysis is performed on comparable VOI values to identify unbalanced comparisons. For example, a student-t test may be applied to a dataset comprised of all VOI values, except those removed on the basis of being incomparable to other VOI values, to identify VOI values which may indicate high radiation dose (e.g., VOI values which differ from a mean VOI value range by at least the first threshold amount).

FIG. 3 shows an example strategy 300 for comparison of VOI values. In the example of FIG. 3, the VOI is a DLP, the benchmark target variable is operators, and the benchmarking context is the past one year as of the date the method is being performed. The example of FIG. 3 is simplified to explain comparison of VOI values; as further described with respect to FIGS. 4-10B, more than one VOI may be compared at a time and additional selections may be made to further specify VOI values to be compared.

In the example of FIG. 3, n operators 302 performed procedures which captured DLP values within the past one year. It is to be understood that there may or may not be additional operators between operator 2 and operator n–1, in some examples. A number of scans performed by each operator may be independent of a number of scans performed by other operators. For example, operator 1 performed four scans which captured DLP values and operator 2 performed two scans which captured DLP values. Some operators may have performed the same amount of scans which captured DLP values, such as operator 1 and operator n–1. In some examples, operators may perform less than two and/or greater than four scans which capture DLP values. Each DLP value captured by a scan is illustrated in FIG. 3 by a box to the right of the respective operator and labeled with a corresponding number (e.g., DLP 1A, DLP 1B, and so on correspond to operator 1), and a letter differentiating scans performed by the same operator (e.g., DLP 1A and DLP 1B are two different scans performed by operator 1).

Lettering among operators is irrelevant to scan types or other scan parameters (e.g., DLP 2A has no inherent correlation to DLP 1A signified by "A").

As described above, matching of observational studies 304 may be performed prior to statistical analysis of VOI values to compare VOI values among comparable studies. Study variables for each DLP value of each operator are compared to study variables for all DLP values of all operators in the past year. For example, study variables used to capture DLP1A (e.g., from operator 1) are compared to study variables used to capture DLP2A, DLP2B, all DLP values from scans performed by operators between operator 2 and operator n–1, DLPn-1A, DLPn-1B, and so on until a final DLP value from a final operator in the benchmarking context (e.g., DLPnC). In some examples, study variables of DLP values may be compared within a set of operator studies (e.g., study variables of DLP1A may be compared to study variables of DLP1B) as well as values from other operator studies. Study variables of DLP values may be sequentially compared to other study variables of DLP values, and comparison may be halted when the same or similar (e.g., within 5% difference for numeric variables) study variables are identified. In some embodiments, study variables of DLP values may be compared all at once and groups of two or more comparable VOI values may be identified among cases having the same or similar (e.g., within 5% difference for numeric variables) study variables. In some instances, study variables used to capture a DLP value may not have a same or similar occurrence within the benchmarking context. In this case, the DLP value which does not have a comparable value may be omitted from statistical analysis. For example, study variables used to capture each of DLP1C and DLPnA may not have comparable study variables within the benchmarking context, thus DLP1C and DLPnA are shown with a line through them at 306, indicating that DLP1C and DLPnA will not be included in the statistical analysis. It is to be understood that all other DLP values within the benchmarking context are comparable with at least one other DLP value.

In some examples, statistical analysis 310 includes performing a one-to-one comparison of a DLP value with a comparable value (e.g., captured from a scan having similar or the same study variables, DLP from the same comparison pair). Each comparison pair may include two DLP values which are not included in other comparison pairs, in some examples. In other examples, some comparison pairs may include the same DLP value. For example, if the study variables of DLP1A, DLP2A, and DLPn-1B are the same as each other and no other cases, a first comparison pair may include DLP1A and DLP2A, and a second comparison pair may include DLP2A and DLPn-1B. Statistical analysis 310 may include determining if a difference between DLP values of a comparison pair is at least the first threshold amount. If the DLP values of the comparison pair do not differ by at least the first threshold amount, then it may be determined that neither of the DLP values in the comparison pair are considerer to indicate a high radiation dose. If the DLP values of the comparison pair differ by at least the first threshold amount, it may be determined that the greater DLP value indicates a high radiation dose. The operator who performed the scan which generated the greater DLP may be considered an outlier operator 312. Information about the outlier operator is output for display on a display device (e.g., the display 128 of FIG. 1), and may be used to identify candidate explanations for the high radiation dose, as further described with respect to FIGS. 4-10B.

As a check to prevent two high radiation dose cases from being in a comparison pair and not being identified as high radiation dose cases (e.g., not being identified as outlier operators 312), in some examples all DLP values are compared for all operators in the past year. For example, DLP1A (e.g., from operator 1) is compared to DLP2A, DLP2B, all DLP values from scans performed by operators between operator 2 and operator n–1, DLPn-1A, DLPn-1B, and so on until DLPnC. In some examples, DLP values may be compared within a set of operator studies (e.g., DLP1A may be compared to DLP1B) as well as values from other operator studies. DLP values may be sequentially compared to other DLP values, and comparison may be halted when a first DLP value differs from a compared to DLP value by at least the first threshold amount in greater than a threshold number of instances. For example, the first DLP value may be compared to three other DLP values with similar study variables and, if it is determined that the difference between the first DLP value and each of the three other DLP values is at least the first threshold amount, the first DLP value may be identified as indicating a high radiation dose and the corresponding operator may be identified as an outlier, to be further discussed with respect to FIG. 4. In some examples, the threshold number of instances may be greater than or less than three instances. In some examples, scans may be performed using a standardized set of study variables, therefore there may be many DLP values which are captured using the same or similar standardized set of study variables. These DLP values may be grouped together to be compared by statistical analysis.

In some examples, statistical analysis 310 is performed on average VOI values for each benchmark target variable subject. For example, following removal of DLP values which do not have a comparable value (e.g., based on matching of study variables) as indicated in FIG. 3 by a line drawn through DLP values, the remaining DLP values for each operator may be averaged 308. Statistical analysis 310 may then be performed on the averaged DLP values. For example, the averaged DLP values may be compared using a student-t test to identify a significance of a difference between means of data sets. Within the student-t test, a first dataset may be the DLP values of the first operator and a second dataset may be the DLP values of the second operator. Significant differences in DLP values may be identified where the difference is at least the first threshold amount. In some examples, there may be groupings of DLP values for each operator, where the DLP values are grouped based on similar study variables. In this case, DLP values may be statistically analyzed within each grouping for an operator. When other operators have groupings of DLP values based on similar study variables, DLP values may be statistically analyzed among operators for values captured using the same or similar study variables. As described above, the greater DLP value may indicate a high radiation dose, and associated operator data may be output for further analysis.

Following statistical analysis of VOI variables and identification of benchmark target variable subjects associated with high radiation doses (e.g., outlier operators 312), candidate explanations are generated for potential causes of the instances of high radiation dose. For example, for a VOI value identified as indicating a high radiation dose, study variables of the scan which generated the VOI value may be compared to standardized study variables to identify potential differences in study variables values which may result in high radiation dose. Further detail regarding candidate explanations and comparison of study variables is described with respect to FIGS. 4-10B.

Turning now to FIG. 4, an example display is shown including a table 400 which may be output for display on a display device (e.g., the display device 128) as a result of executing operation 204 of the method 200. For example, the table 400 may be generated following statistical analysis 310 of FIG. 3, and information about the one or more outlier operators 312 is included in the table 400. The table 400 shows results of a comparison of operator practices (e.g., "operators" is the benchmark target variable/population) for two protocols (e.g., "protocols" is the benchmarking context, specifically a first protocol and a second protocol). The table 400 further includes candidate explanations indicating why an operator was identified by the method as having a high radiation dose. The table 400 is an example of how information from the statistical analysis may be organized and presented for display on a display device, however other displays may be generated and displayed without departing from the scope of the present disclosure.

A first header 402 and a second header 404 include information about the benchmarking context. In the example of FIG. 4, the first header 402 includes information about a first protocol, which is a standard brain scan performed in facility one by eight operators. The second header 404 includes information about a second protocol, which is an axial brain scan performed in facility one by 281 operators. The 281 operators who performed the second protocol may or may not include at least one of the eight operators who performed the first protocol, and vice versa. In other examples, there may be more than or less than two headers, and each header may include information about different benchmarking context, compared to FIG. 4. For example, when the benchmarking context is studies from the past year and the benchmark target variable is hospitals, the first header may be a first month or a first quarter, the second header may be a second month or a second quarter, a third header may be a third month or a third quarter, and so on.

A first column 406 under each of the first header 402 and the second header 404 identifies at least one operator 410 which has been identified as having a high radiation dose (e.g., radiation dose which differs from a desired radiation dose by at least the first threshold amount). In the example of FIG. 4, the first column 406 shows an operator's name, however in other examples a different identifier may be used, such as an identification number or operator code. As described with respect to FIG. 3, operators who performed scans which had high radiation doses may be identified by comparing the variable of interest of a first operator to variables of interest of all other operators within the benchmarking context.

A second column 408 under each of the first header 402 and the second header 404 indicates, for each operator identified in the first column 406, at least one candidate explanation 412 for the high radiation dose. Candidate explanations may include analyses about parameters of the protocol used to capture the VOI value, characteristics of the device used to perform the protocol, and/or patient characteristics. An up arrow may be positioned next to a parameter in the second column 408 to indicate the parameter may be high (e.g., total number of irradiations is higher than average total number of irradiations for protocols performed by other operators). In other examples, a down arrow may be positioned next to the potential parameter to indicate the parameter may be low. In some examples, the first indicator may be something other than an icon, for example, a text side, boldness, color, font, and so on may be adjusted to indicate the potential parameter state (e.g., high/low).

For the first protocol (e.g., under the first header 402), Operator 1 is the only operator of the eight operators who performed the first protocol to be identified as performing a scan which has a high radiation dose. For example, a first radiation dose received by a first patient as a result of the first procedure, performed by Wagner, may be greater than a second radiation dose received by a second patient as a result of either the first procedure or the second procedure, either of which performed by an operator, which may include Wagner. The first radiation dose (e.g., identified as a high radiation dose) may be greater than the compared to radiation dose by at least the first threshold amount. For example, the first radiation dose may be 10 mGy*cm greater than the second radiation dose. As shown in the second column 408, a candidate explanation for identifying Wagner's scan as having a high radiation dose may be that a study total DLP for Wagner's scan may be high to compare to study DLP values of other operators within the first protocol group and the second protocol group. As briefly described above and further described with respect to FIGS. 5-10B, more than one VOI may be selected when initiating the method 200. Thus, more than one VOI are shown in the second column 408 for some of the operators in the first column 406. For example, additional candidate explanations for Operator 1 include a high total number of irradiations for the study, a high spiral total number of irradiations, and a high spiral CTDI.

For some potential parameters, such as is shown with the high spiral CTDI in the case of the first operator, a second indicator may be shown to indicate a potential adjustment which may be made to the potential parameter to adjust the outcome of future protocol executions (e.g., lower the dose). For example, the second indicator may be a wrench and may be positioned next to, in front of, or after the potential parameter and may be followed by text indicating an adjustment which may be made to adjust the potential parameter. For example, to decrease spiral CTDI for Operator 1, it is proposed that a pitch factor be adjusted, where the pitch factor for single slice CT systems is a distance that a table (e.g., of a CT system on which an imaging subject may be positioned) travels in one 360-degree gantry (e.g., of the CT system) rotation, divided by beam collimation. The pitch factor affects both image quality and radiation dose, where a pitch factor of greater than one decreases patient dose and may also decrease image quality, as fewer projections are obtained, and a pitch factor less than one may increase radiation dose and increase image quality, as more projections are obtained. Under the second header 404 for Operator 2, adjusting an average x-ray tube current/exposure is provided as a potential adjustment which may address the sequenced CTDI being high.

To further analyze candidate explanations for identified high radiation doses and potential adjustments which may be made to reduce the radiation dose, a subject may be selected for further study. For example, a user may select data associated with Operator 1 for further analysis by selecting at least one of the operator's name (e.g., from the first column 406) and/or a candidate explanation (e.g., from the second column 408). A causal graph may be generated which shows relationships among study variables used to generate the VOI value of interest. For example, values of study variables used to generate the VOI value of interest may be compared to standard study variable values used to perform the same scan. For example, standard study variable values may be industry standards, hospital/healthcare provider standards, device standards, and so on which may be a default value used for each scan. For some scans, such as when a patent is larger than an average patient size, study variable values may be adjusted from the standard. In some cases, this may result in an increase in radiation dose, as indicated by the identified VOI.

Turning to FIG. 5, a causal graph 500 is shown. The causal graph 500 is for a computed tomography (CT) case and includes study variables used to perform a CT scan. Directional connectors between labeled nodes for each study variable indicate relationships among the study variables. For example, in the causal graph 500, a patient age node, an operator node, and a BMI node all point to a protocol node. This indicates that a probability distribution of the protocol node (e.g., a child node) is dependent on values of the parent age node, the operator node, and the BMI node (e.g., parent nodes). Given values of the parent node(s), the child node is independent of non-descendants. For example, once values of the protocol node are known, values of a parameter node are influenced by values of the protocol node and not by values of the patient age node, the operator node, and/or the BMI node. Similarly, once values of the BMI node are known, values of the parameter node are not influenced by values of a patient size node or a patient weight node. The causal graph defines a general probability structure and is used to specify joint distribution.

Briefly returning to FIG. 4, selecting "spiral CTDI" in the second column 408 under the first header 402 for Operator 1 may generate the causal graph 500. Information regarding study variables used to capture the identified VOI may be retrieved from a radiation database, such as the RDD 116 of the RMS 114 of FIG. 1. Retrieved study variable information may be compared to standard study variable values to identify potential deviation from the standard. In some cases, there may be a study variable which is identified as differing from a standard study variable value by at least a second threshold amount. For example, the second threshold amount may be an amount which may increase a radiation dose. In other examples, the study parameters for the identified VOI value may be compared to average values of respective parameters for comparable VOI values.

Following analysis of study variables used to generate the CTDI, generation and output of the causal graph 500 may indicate that the CTDI (e.g., indicated by a CTDI node) is influenced by parameters and a device model. As shown in FIG. 5, nodes of study variables which are determined to directly influence the CTDI may be directly connected to the CTDI node. In some examples, study variables determined to directly influence the CTDI may additionally be indicated on the causal graph, for example, by a color, pattern, and/or other visual indicator. The parameters are influenced by the device model, patient BMI, the protocol, and the operator. Thus, adjustments to any nodes which directly influence the CTDI, and/or adjustments to nodes which influence nodes that directly influence the CTDI may result in adjustment to the CTDI. In this way, the causal graph is an example of an exploratory medium which may be modified to simulate possible adjustments to study variables without performing a simulated scan using an imaging device. In some examples, as further described herein, study variable values for one or more imaging studies may be automatically updated based on an updated causal graph which has been updated to simulate potential adjustments which may change (e.g., increase or decrease) a respective VOI value.

Figure 6:
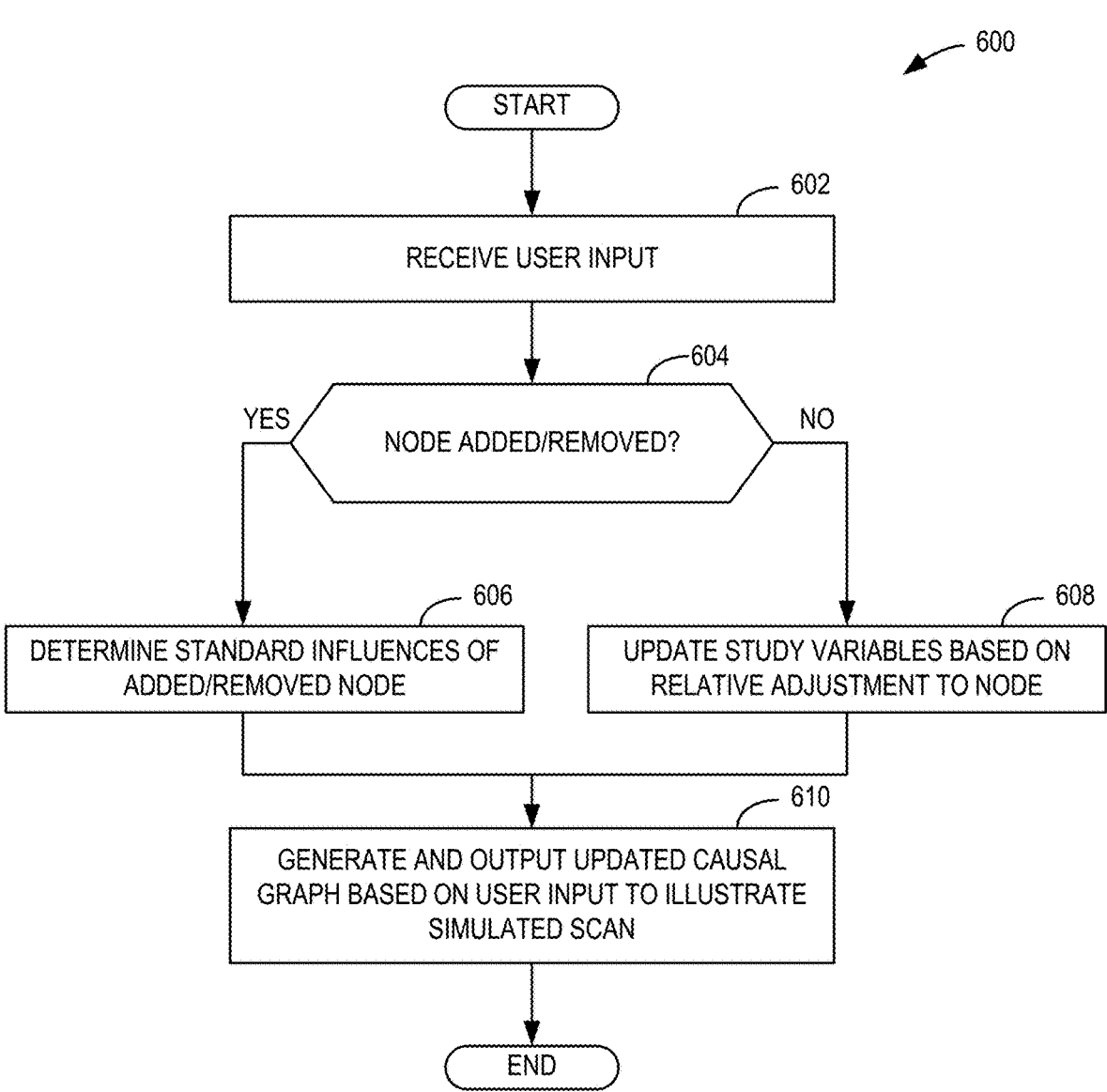
FIG. 6 illustrates a high-level method for updating a causal graph based on user input.

FIG. 6 illustrates a high-level method 600 for automatically generating a causal graph, based on received user input to add, remove, or otherwise adjusting at least one study variable, to show a potential causal graph of a simulated scan having updated study variables. At 602, the method 600 includes receiving a user input, which includes adjustment to at least one parameter of a causal graph. For example, the causal graph 500 may be displayed on a display device (e.g., the display device 128 of FIG. 1) and a user may interact with a GUI (e.g., the GUI 126 of FIG. 1) to make adjustments to the causal graph 500. Adjustments may include adding and/or removing at least one node of the causal graph, and/or adjusting a value of a study parameter via a respective node on the causal graph.

If at 604 it is determined that a node is added and/or removed, the method 600 proceeds to 606 to determine standard influences of the added/removed node. For example, when a node is removed, and the removed node had at least one parent node and at least one child node in the initial causal graph (e.g., the causal graph 500), the parent node may connect directly to the child node in the resulting updated graph (e.g., where the removed node is no longer an intermediate therebetween). When a node is added, a radiation dose data base (e.g., the RDD 116 of FIG. 1) may be searched for scans which include the study variables of the causal graph and the study variable of the added node. An influence of the added node (e.g., whether the added node directly or indirectly influences the VOI) may be inferred based on influence of the study variable of the added node in scans stored in the radiation dose database, and the inferred influence may be added to the updated causal graph. In other examples, relationships among study variables may be stored in the RDD and retrieved from the RDD by the analytics tool in response to determining a node has been added and/or removed from the causal graph.

If at 604 it is determined that a node is not added and/or removed from the causal graph, the method proceeds to 608 to update one or more study variables of the causal graph based on a relative adjustment to the node. If at least one node is not added and/or removed, it is assumed that the user input include adjusting a value of at least one status variable. For example, a user may select the parameters node of the causal graph 500, selection of which generates a window on the display including a list of parameter values, such as pitch factor. The input may include changing the pitch factor from 1 to 1.5, for example. As briefly described above, the pitch factor affects both image quality and radiation dose, where a pitch factor of greater than one decreases patient dose and may also decrease image quality, as fewer projections are obtained. Based on known relationships among study variables which, for example, may be stored in the memory 132 of the analytics tool and/or in the RDD 116, other study variables of the causal graph may be updated accordingly. For example, an increase in the pitch factor may result in a decrease in the CTDI.

From operations 606 and 608, the method 600 proceeds to 610, where the method 600 includes generating and outputting an updated causal graph, based on the user input, to illustrate a simulated scan. An updated causal graph is said to illustrate a simulated scan, as the updated causal graph shows potential influences of study variables on a VOI, however a scan is not simulated by a hospital modality, such as an imaging device 102 of FIG. 1. In this way, generating updated causal graphs based on user input enables visualization of factors (e.g., study variables) in a way that allows users to see potential influences of each factor and thus more easily select which factors to modify to achieve a desired result (e.g., decrease a high radiation dose). Examples of updated causal graphs are shown in FIGS. 7-9.

In one example, adjustment to the causal graph 500 includes removal of one or more nodes. Upon removal of a node, parent nodes of the removed node may be directed to child nodes of the removed node. Turning to FIG. 7, a first updated causal graph 700 is shown, where the first updated causal graph 700 is an updated version of the causal graph 500 of FIG. 5. The causal graph 500 indicates that the CTDI may be directly influenced by the device model and the parameters, and the parameters are directly influenced by the BMI. Thus, the CTDI may be indirectly influenced by the BMI. In the example of FIG. 7, the BMI node has been removed, and the causal graph 500 has been automatically updated to direct the patient size node and the patient weight node to the protocol node, the parameters node, and the image quality (IQ) node. Connections among all other nodes may be unchanged.

In another example, adjustment of the causal graph 500 includes addition of one or more node. One or more parent nodes and/or one or more child nodes for the added node may be manually added, such as through input from a user. Turning to FIG. 8, a second updated causal graph 800 is shown, where the second updated causal graph 800 is an updated version of the causal graph 500 of FIG. 5. In the example of FIG. 8, a radiation exposure node, which provides information about prior patient exposure to radiation, is added. The radiation exposure node may manually (e.g., via user input) or automatically (e.g., based on a configuration of the causal graph 500) be connected to the protocol node and to the parameters node. For example, automatic connection of added nodes, such as the radiation exposure node, may be performed when the node to be added is selected from a library of pre-stored nodes, each having known connections among other nodes of the causal graph. Following addition of the node, the causal graph 500 is automatically updated to display the added node and new connections in the second updated causal graph 800. Because additional patient information is provided by including the radiation exposure node, the BMI node is shown as influencing only the image quality. Patient size is still shown influencing protocol, for example, a different protocol may be chosen for someone at or less than 5 ft tall than is chosen for someone greater than 5 ft tall.

In a further example, adjustment of the causal graph 500 includes adjusting a value of at least one study variable. FIG. 9 shows a third updated causal graph 900, which is an updated version of the causal graph 500 following user input. In the example of FIG. 9, a value of the parameter node has been changed. Specifically, as shown in a window 902, a pitch factor has been increased (e.g., an up arrow 904). As a result of increasing the pitch factor, and relationships among causal graph nodes including between the parameters node and the CTDI node, the third updated causal graph 900, which shows simulated results of a scan performed using the adjusted study variable values, the CTDI value is decreased (e.g., a down arrow 906).

Each of the causal graph 500, the first updated causal graph 700, and the second updated causal graph 800, and the third updated causal graph 900 may be generated based on user interaction with a GUI, such as the GUI 126 of FIG. 1, and displayed on a display device, such as the display device 128 of FIG. 1. Use of a causal graph to represent potential influences of different study variables on a radiation dose amount (e.g., represented by a VOI) provides a visual representation of how the study variables are causally linked to the resulting VOI. By automatically updating the causal graph (e.g., from the causal graph 500 to the first updated causal graph 700) following user input, statistical interactions of different factors are shown, which enables users with an efficient way to use a graphical interface (e.g., the GUI 126 of FIG. 1) to visualize factors (e.g., study variables) in a way that allows users to more easily select which factors to modify. Following modification of a causal graph, a new (e.g., updated) simulated causal graph is automatically updated, thus showing potential influences of the study variables in near-real time. The causal graphs described herein illustrate to a user, via nodes and connections therebetween, how study variables influence and are influenced by each other. The connections between nodes show how real-world parameters used to conduct imaging scans statistically affect other real-world parameters also used to conduct imaging scans, as well as resulting effects of the scan, such as radiation dose received by a patient.

A method 1000 for automatic benchmarking for radiology is illustrated in FIGS. 10A-10B. The method 1000 includes identifying instances of high radiation dose, generating candidate explanations, and generating and automatically updating causal graphs. Instructions for the method 1000 may be stored in a memory of an analytics tool, such as the memory 132 of the analytics tool 122 of FIG. 1, and executed by a processor thereof (e.g., the processor 130). The processor 130 may receive inputs/requests/selections, as described herein, which may be input by a user via a GUI (e.g., the GUI 126 of the client device 124 of FIG. 1).

At 1002, the method 1000 includes receiving a first user input. The first user input includes selection of at least one (e.g., one or more) VOI, a benchmark target variable, and a benchmarking context. Elements of the first user input may be selected via user interaction with a user interface, such as the GUI 126 of FIG. 1.

At 1004, the method 1000 includes comparing values of the at least one VOI for a first subject of the benchmark target variable with values of the same VOI from other subjects of the benchmark target variable within the benchmarking context to identify VOI values which differ by at least the first threshold amount from other VOI values of the same VOI. For example, as described with respect to FIGS. 2-3, a first DLP value captured by a first operator may be compared to DLP values captured by a second operator, a third operator, and so on. Comparing values includes matching observational studies (e.g., used to capture the first DLP value) by comparing study variables (e.g., patient age, size, gender, and so on) among scans in order to determine differences in VOI values among comparable studies. The "first subject" is to be understood in operation 1004 as identifying a single subject having at least one VOI which is compared to VOI of other subjects of the same benchmark target variable. As described below with respect to operation 1028, the method 1000 is repeated for all subjects of the benchmarking target variable, thus the "first subject" may be the subject of the VOI being compared.

At 1006, the method 1000 includes determining if the compared VOI values differ by greater than the first threshold amount. If compared VOI do not differ by at least the first threshold, it is determined at 1026 that neither of the compared VOI may indicate a high radiation dose. At 1028, the method 1000 includes returning to operation 1004 and repeating the method 1000 for all VOI values from all benchmark target variable subjects within the benchmarking context.

For the VOI values identified as differing by at least the first threshold amount, at 1008, it is determined that a higher value VOI of the compared VOIs may indicate a high radiation dose. At 1010, the method 1000 includes generating and outputting for display an output including a subject identifier and at least one candidate explanation for the identified VOI value. An example output is shown and described with respect to FIG. 4. The subject identifier may be a name, identification number or code, or other identifying information for an operator, device, hospital, or other benchmark targeting variable. The candidate explanation may include a brief statement about a study variable and an indication of relative influence. For example, in the example of Operator 1 in FIG. 4, the identified VOI may be caused by the study total number of irradiations being relatively high. Identification of candidate explanations may be performed as described herein, by comparing study variable values with standardized study variable values and/or study variable values of comparable VOI values, for example.

At 1012, the method 1000 includes returning to operation 1004 and repeating the method 1000 for all VOI values from all benchmark target variable subjects within the benchmarking context. In this way, multiple VOIs may be identified as differing from a compared to VOI by at least the first threshold, and information about each identified VOI may be included in the same or in different outputs (e.g., FIG. 4, including subject identifier and at least one candidate explanation). Additionally, the first user input may include selection of more than one VOI, and the method 1000 may be repeated to compare VOI values of all selected VOI types (e.g., DLP, CTDI, and so on) as described herein with respect to DLP and CTDI (e.g., in FIGS. 2-4). Subject identifiers and candidate explanations for VOI values of different types may be included in the same or in different outputs. For example, the table 400 of FIG. 4 includes information about CTDI and DLP values.

Following comparison of VOI values for all VOIs from all subjects of the benchmarking target variable within the benchmarking context, at 1014, the method 1000 includes receiving a second user input selecting a subject of the benchmarking target variable from the output (e.g., table 400 of FIG. 4) by selecting the respective subject identifier. A subject may be selected for further analysis, such as comparison of study variables and/or exploration of candidate explanations using a causal graph. If the selected subject has more than one associated VOI, a separate causal graph may be generated for each VOI value.

At 1016, the method 1000 includes comparing study variables used to generate the identified VOI (e.g., of the selected subject) to average values of respective study variables of comparable VOI values. For example, study variables of scans used to capture comparable VOI values may be stored in a radiation dose database and referenced to identify study variables having values which differ between the identified VOI and comparable VOI by at least the second threshold amount. As described with respect to FIGS. 5-9, study variables of the identified VOI which differ from study variables of the comparable VOI by at least the second threshold amount may directly influence the VOI in a way that results in a high radiation dose.

At 1018, the method 1000 includes generating and outputting a causal graph indicating one or more study variables of the identified VOI which differ from study variables of comparable VOI by at least the second threshold amount. In some examples, such as those described with respect to FIGS. 5-9, the differing study variable(s) may be indicated by a direct connection between the differing study variable(s) and the VOI (e.g., without a node therebetween). In other examples, the differing study variable(s) may be identified by a different shading, coloring, shape, pattern, and so on of the respective node and/or connector between the respective node and other nodes (e.g., study variables/the VOI).

At 1020, the method 1000 includes receiving a third user input, which includes adjustment to at least one study variable of the causal graph (e.g., causal graph 500 of FIG. 5). As described with respect to FIGS. 5-9, adjustment may include adding one or more nodes (e.g., adding one or more study variables), removing one or more nodes (e.g., removing one or more study variables), and/or adjusting values of one or more study variables. The user may provide the third user input by interacting with a user interface, such as the GUI 126 of FIG. 1. Additional study variables may be selected from a library of study variables stored on a memory, such as the memory 132, where the study variables are stored along with predefined relationships with other study variables, such that when a study variable is added to a causal graph, connections to other study variable nodes are made automatically.

At 1022, the method 1000 includes updating the causal graph based on the third user input. For example, as described with respect to FIGS. 5-9, an updated causal graph may represent influences of study variables (e.g., both those adjusted at operation 1020 and non-adjusted study variables of the causal graph) on a VOI in a simulated scan. With the adjustments to at least one study variable, connections representing study variable influences on each other and the VOI may change. For example, some study variables may no longer directly influence the VOI.

At 1024, the method 1000 includes outputting the updated causal graph for display on the display device (e.g., display device 128). In some examples, the updated causal graph may be further updated by additional user inputs to add and/or remove nodes, and/or adjust values of study variables, to provide a visualization of influences of study variables on a VOI.

In some examples, the update causal graph may be used to inform and or initiation actions of one or more devices coupled to the analytics tool used to generate the updated causal graph. At 1030, the method 1000 includes transmitting study variable values of the updated causal graph to automatically update imaging study parameters for the respective benchmark target variable subject. For example, information from the updated causal graph, such as additional study variables, may be transmitted via a wired and/or wireless connection operably coupling the analytics tool to an imaging device to set parameters for an imaging procedure. As described with respect to FIG. 8, a node may be added in the updated causal graph representing prior radiation exposure of the patient. In response, a parameter of an imaging procedure for the respective patient may automatically be updated to reduce an amount of radiation output by the imaging device. As another example, the method 1000 may identify an operator of the group of operators (e.g., the benchmark target variable) who uses a first set of study variable values for an imaging study, which results in a VOI value which differs from VOI values of comparable studies by at least the first threshold amount (e.g., the identified VOI value). One or more study variable values may be adjusted from the first set of study variables by modifying the causal graph, such that the updated causal graph has a second set of study variable values with one or more study variable values differing from the first set of study variable values. The second set of study variable values may be sent to the imaging device (e.g., the imaging device 102 of FIG. 1) and/or stored in associated with an identifier of the operator (e.g., stored in the RDD 116 of FIG. 1) such that when the operator orders and/or conducts a new imaging scan, the second set of study variables are automatically used, or the user is prompted to select the second set of study variables.

In this way, adjustments to imaging protocols may be made automatically, based on identified trends in benchmark target variable subjects and VOI values, which may reduce a workload on an operator and may help provide radiation doses which are within a desirable range to patients.

Generation and automatic updating of one or more causal graphs as described herein is used to provide a visual representation of how study variables, including those which may (e.g., protocol parameters, imaging device) or may not be adjustable (e.g., patient age, size, weight, and so on) may influence a radiation dose delivered, and how changes to the study variables affect a radiation dose. The methods and systems described herein may thus assist a healthcare provider in identifying study variable parameters and values which may enable a radiation dose to remain within a desired level for a given patient and/or scan. Adjustments may be made to study variables to simulate scans and identify study variable values without running multiple imaging scans and potentially exposing both operators and patients to unnecessary radiation doses.

The disclosure also provides support for a medical system, comprising: a client device having a graphical user interface (GUI) and a display device, the client device operably coupled to a network, and an analytics tool configured with instructions stored on a memory and executable by a processor to receive a first user input via the client device, identify values of at least one variable of interest (VOI) from a subject of a benchmark target variable which differ by at least a first threshold amount from other values of the same VOI from other subjects of the benchmark target variable within a benchmarking context, generate and output for display on the display device a causal graph illustrating influences of different study variables on an identified VOI value, and automatically update the causal graph and display thereof based on a second user input to adjust at least one study variable. In a first example of the system, the first user input is input into the client device via the GUI and includes selection of one or more VOI indicating a relative radiation dose level, the benchmark target variable defining a population to be studied, and the benchmarking context defining a target set of historical studies to be compared. In a second example of the system, optionally including the first example, the system further comprises: an imaging device operably coupled to the analytics tool and configured to receive information from an updated causal graph and automatically adjust parameters of an imaging protocol based on information from the updated causal graph. In a third example of the system, optionally including one or both of the first and second examples, study variable standards, the value of the at least one VOI and associated study variables, and information regarding relationships among study variables is stored in a radiation dose database (RDD) operably coupled to the analytics tool via the network. In a fourth example of the system, optionally including one or more or each of the first through third examples, generating the causal graph includes retrieving study variable standards from the RDD, comparing study variables used to capture the identified VOI value to the study variable standards, identifying one or more study variables used to capture the identified VOI value which differ from the respective study variable standards by at least a second threshold amount, and directly connecting a node representing each of the one or more differing study variables to a node representing the identified VOI value. In a fifth example of the system, optionally including one or more or each of the first through fourth examples, generating the causal graph further includes retrieving information regarding relationships among study variables from the RDD, generating a node for each of the study variables used to capture the identified VOI value which do not differ from the respective study variable standards by at least the second threshold, and connecting the nodes to each other and to the node representing the identified VOI value based on the information regarding relationships among study variables. In a sixth example of the system, optionally including one or more or each of the first through fifth examples, the second user input is input into the client device via the GUI and includes at least one of addition of a study variable to the causal graph, removal of a study variable from the causal graph, and/or adjustment to a value of a study variable of the causal graph. In a seventh example of the system, optionally including one or more or each of the first through sixth examples, automatically updating the causal graph and display thereof includes retrieving information regarding relationships of the added, removed, and/or adjusted study variables from the RDD, adding and/or removing one or more nodes representing the respective added and/or removed study variables, and adjusting connections among nodes of the causal graph to illustrate influences of each study variable on the identified VOI.

The disclosure also provides support for a method, comprising: comparing a variable of interest (VOI) value from a first subject of a benchmark target variable with values of the same VOI from other subjects of the same benchmark target variable within a benchmarking context, identifying a VOI value which differs from a comparable VOI value by at least a first threshold, generating at least one candidate explanation for the difference in VOI values, generating a causal graph illustrating at least one candidate explanation for the difference in VOI values, and automatically updating the causal graph to incorporate adjustments to nodes of the causal graph to simulate a radiation dose delivery. In a first example of the method, comparing the VOI value from the first subject includes comparing study variables used to capture the VOI value to study variables used to capture other VOI values of the same VOI from other subjects to identify comparable VOI values, and comparing the VOI value from the first subject to comparable VOI values from other subjects having the same or similar study variable values. In a second example of the method, optionally including the first example, comparing the VOI value from the first subject to other VOI values from the same VOI from other subjects includes comparing the VOI value from the first subject to a first average VOI value comprised of all comparable VOI values from a second subject, to a second average VOI value comprised of all comparable VOI values from a third subject, and so on. In a third example of the method, optionally including one or both of the first and second examples, generating at least one candidate explanation includes comparing values of study variables used to capture an identified VOI which differs from a comparable VOI value by at least the first threshold to study variable standards, and identifying one or more study variables used to capture the identified VOI value which differs from the respective study variable standards by at least a second threshold amount. In a fourth example of the method, optionally including one or more or each of the first through third examples, generating the causal graph illustrating at least one candidate explanation for the difference in VOI values includes generating a plurality of nodes, each of which represents a study variable of the study used to generate the identified VOI, and connections among the nodes representing an influence of each node on other nodes, including the node representing the VOI. In a fifth example of the method, optionally including one or more or each of the first through fourth examples, one or more nodes, each representing study variables of the identified VOI which differ from study variable standards by at least the second threshold amount, are directly connected to the node representing the VOI. In a sixth example of the method, optionally including one or more or each of the first through fifth examples, automatically updating the causal graph includes adding and/or removing at least one node representing a study variable, and connections to/from the added and/or removed node to other nodes of the causal graph, based on information regarding relationships among study variables.

The disclosure also provides support for a method, comprising: receiving a first user input, including selection of at least one variable of interest (VOI), a benchmark target variable, and a benchmarking context, for the at least one VOI, comparing values of the VOI for a first subject of the benchmark target variable with values of the same VOI from other subjects of the benchmark target variable within the benchmarking context to identify VOI values which differ by at least a first threshold amount from other VOI values of the same VOI, for the VOI values identified as differing by at least the first threshold amount, generating and outputting for display an output including a subject identifier and at least one candidate explanation for the identified VOI value, receiving a second user input selecting a subject from the output by selecting the respective subject identifier, comparing study variables used to generate the identified VOI value to average values of respective study variables of comparable VOI values, and generating and outputting for display a causal graph indicating at least one study variable of the study variables used to generate the identified VOI which differs by at least a second threshold amount, receiving a third user input including an adjustment to at least one study variable of the causal graph, wherein adjustment includes adding and/or removing at least one study variable node, and/or adjusting a value of the at least one study variable node, updating the causal graph based on adjustments included in the third user input, and outputting the updated causal graph for display on a display device. In a first example of the method, the VOI indicates a radiation dose level and is one of a dose length product (DLP), a computed tomography dose index (CTDI), a size specific dose estimate (SSDE), and/or an image quality related to a radiation dose. In a second example of the method, optionally including the first example, the benchmark target variable defines a population and is one of operators, hospitals, and hospital modalities. In a third example of the method, optionally including one or both of the first and second examples, the benchmarking context defines a target set of historical studies to be compared and is one of a timeframe, as a distance, and/or an amount of locations and/or devices. In a fourth example of the method, optionally including one or more or each of the first through third examples, generating the output including the subject identifier and at least one candidate explanation for the identified VOI value includes comparing values of study variables used to capture the identified VOI to study variable standards, and identifying one or more study variables used to capture the identified VOI value which differs from the respective study variable standards by at least a second threshold amount.

As used herein, an element or step recited in the singular and preceded with the word "a" or "an" should be understood as not excluding plural of said elements or steps, unless such exclusion is explicitly stated. Furthermore, references to "one example" of the present invention are not intended to be interpreted as excluding the existence of additional examples that also incorporate the recited features. Moreover, unless explicitly stated to the contrary, examples "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical system, comprising:
a client device having a graphical user interface (GUI) and a display device, the client device operably coupled to a network;
an imaging device; and
an analytics tool operably coupled to the imaging device and configured with instructions stored on a memory and executable by a processor to:
receive a first user input via the client device,
identify values of at least one variable of interest (VOI) from a subject of a benchmark target variable which differ by at least a first threshold amount from other values of the same VOI from other subjects of the benchmark target variable within a benchmarking context, wherein identifying the values of the at least one VOI from the subject of the benchmark target variable which differ by at least the first threshold amount comprises matching the at least one VOI from the subject with the other values of the same VOI from the other subjects having similar study variables and performing a statistical analysis to identify the at least one VOI which differ by at least the first threshold amount,
identify a candidate explanation of why the values from the subject of the benchmark target variable differs from the other values from the other subjects of the benchmark target variable,
generate and output for display on the display device a causal graph illustrating influences of different study variables on an identified VOI value, wherein nodes of the causal graph each represent a factor of the different study variables, wherein the different study variables comprise patient characteristics, device characteristics, operator, protocol, and parameters of the protocol,
automatically update the causal graph and display thereof in real time, based on a second user input to adjust at least one study variable of the different study variables, and
transmit study variable values of the updated causal graph to the imaging device, wherein the updated causal graph illustrates a simulated scan;

wherein the imaging device is a computed tomography system or an x-ray angiography system, operably configured to:

receive the transmitted study variable values of the updated causal graph, automatically update imaging study parameters of an imaging procedure based on the updated causal graph, perform the imaging procedure using the updated imaging study parameters of the imaging procedure to achieve a desired VOI value, and send radiation dose data of the imaging procedure to the analytics tool.

2. The medical system of claim 1, wherein the first user input is input into the client device via the GUI and includes selection of one or more VOI indicating a relative radiation dose level, the benchmark target variable defining a population to be studied, and the benchmarking context defining a target set of historical studies to be compared.

3. The medical system of claim 1, wherein study variable standards, the value of the at least one VOI and associated study variables, and information regarding relationships among study variables is stored in a radiation dose database (RDD) operably coupled to the analytics tool via the network.

4. The medical system of claim 3, wherein generating the causal graph includes retrieving study variable standards from the RDD, comparing study variables used to capture the identified VOI value to the study variable standards, identifying one or more study variables used to capture the identified VOI value which differ from the respective study variable standards by at least a second threshold amount, and directly connecting a node representing each of the one or more differing study variables to a node representing the identified VOI value.

5. The medical system of claim 4, wherein generating the causal graph further includes retrieving information regarding relationships among study variables from the RDD, generating a node for each of the study variables used to capture the identified VOI value which do not differ from the respective study variable standards by at least the second threshold, and connecting the nodes to each other and to the node representing the identified VOI value based on the information regarding relationships among study variables.

6. The medical system of claim 1, wherein the second user input is input into the client device via the GUI and includes at least one of addition of a study variable to the causal graph, removal of a study variable from the causal graph, and/or adjustment to a value of a study variable of the causal graph.

7. The medical system of claim 6, wherein automatically updating the causal graph and display thereof includes retrieving information regarding relationships of the added, removed, and/or adjusted study variables from a radiation dose database, adding and/or removing one or more nodes representing the respective added and/or removed study variables, and adjusting connections among nodes of the causal graph to illustrate influences of each study variable on the identified VOI.

8. The system of claim 1, wherein identifying the values of the at least one variable of interest (VOI) from the subject of the benchmark target variable which differ by at least the first threshold amount comprises matching the at least one VOI from the subject with the other values of the same VOI from the other subjects having similar study variables and performing a statistical analysis to identify the at least one VOI which differ by at least the first threshold amount.

9. The system of claim 1, wherein a first study variable is identified as the candidate explanation when the first study variable has a statistically significant effect on the VOI.

* * * * *